(12) United States Patent
Doucette et al.

(10) Patent No.: US 9,592,500 B2
(45) Date of Patent: Mar. 14, 2017

(54) FILTRATION AND EXTRACTION ASSEMBLY

(71) Applicant: Dalhousie University, Halifax (CA)

(72) Inventors: Alan A. Doucette, Stillwater Lake (CA); Mark James Wall, Halifax (CA)

( * ) Notice: Subject to any disclaimer, the term of this patent is extended or adjusted under 35 U.S.C. 154(b) by 0 days.

(21) Appl. No.: 14/388,625

(22) PCT Filed: May 9, 2013

(86) PCT No.: PCT/CA2013/050360
§ 371 (c)(1),
(2) Date: Sep. 26, 2014

(87) PCT Pub. No.: WO2013/166605
PCT Pub. Date: Nov. 14, 2013

(65) Prior Publication Data
US 2015/0051383 A1    Feb. 19, 2015

Related U.S. Application Data

(60) Provisional application No. 61/644,473, filed on May 9, 2012.

(51) Int. Cl.
*B01L 3/00*      (2006.01)
*G01N 1/40*      (2006.01)
(Continued)

(52) U.S. Cl.
CPC ........ *B01L 3/5021* (2013.01); *B01D 17/0217* (2013.01); *B01L 3/00* (2013.01); *B01L 3/502* (2013.01); *B01L 3/50825* (2013.01); *G01N 1/34* (2013.01); *G01N 1/405* (2013.01); *G01N 1/4077* (2013.01); *A61M 1/3693* (2013.01);
(Continued)

(58) Field of Classification Search
CPC .... G01N 1/34; G01N 1/405; G01N 2030/009; G01N 2030/062; G01N 2030/8831; G01N 1/4077; G01N 2001/4061; G01N 2001/4088; B01D 27/00; B01D 35/02; B01D 25/02; B01D 29/05; B01D 29/58; B01D 21/26; B01D 21/262; B01D 61/18; B01D 2221/10; B01D 17/0217; B01L 3/00; B01L 3/502; B01L 3/5021; B01L 3/50825; B01L 2300/042; B01L 2300/0681; B01L 2200/0631; B01L 2400/0409; A61M 1/3693
See application file for complete search history.

(56) References Cited

U.S. PATENT DOCUMENTS 5,219,529 A * 6/1993 Ngo ..................... B01D 35/303
                                                      206/534
5,601,711 A * 2/1997 Sklar ..................... B01D 25/02
                                                      210/232
(Continued)

FOREIGN PATENT DOCUMENTS

JP    WO 2011158738 A1 * 12/2011 ............. G01N 1/405
WO    WO 0260556     * 1/2002
WO    02060556       8/2002

*Primary Examiner* — Katherine Zalasky
*Assistant Examiner* — Benjamin Lebron
(74) *Attorney, Agent, or Firm* — Ryan W. Dupuis; Kyle R. Satterthwait; Ade & Company Inc.

(57) ABSTRACT

Among other things, in general, a two-stage filtration and extraction assembly is described, as well as methods of use thereof.

3 Claims, 13 Drawing Sheets

(51) Int. Cl.
*B01D 17/02* (2006.01)
*G01N 1/34* (2006.01)
*A61M 1/36* (2006.01)
B01D 27/00 (2006.01)
G01N 30/00 (2006.01)

(52) U.S. Cl.
CPC .......... *B01D 27/00* (2013.01); *B01D 2221/10* (2013.01); *B01L 2200/0631* (2013.01); *B01L 2300/042* (2013.01); *B01L 2300/0681* (2013.01); *B01L 2400/0409* (2013.01); *G01N 2001/4061* (2013.01); *G01N 2001/4088* (2013.01); *G01N 2030/009* (2013.01)

(56) References Cited

U.S. PATENT DOCUMENTS

| | | | | |
|---|---|---|---|---|
| 6,622,882 B2* | 9/2003 | Smith | ................ | B01L 3/50825 |
| | | | | 215/253 |
| 6,770,246 B1* | 8/2004 | Husek | ................... | B01L 3/0275 |
| | | | | 210/263 |
| 2002/0041938 A1* | 4/2002 | Takahashi | ................ | B01J 20/26 |
| | | | | 428/34.1 |
| 2005/0003450 A1* | 1/2005 | Rush | ...................... | C07K 14/47 |
| | | | | 435/7.1 |
| 2007/0212738 A1* | 9/2007 | Haley | ................ | G01N 33/5011 |
| | | | | 435/7.23 |
| 2008/0287661 A1* | 11/2008 | Jones | ................... | B01L 3/0275 |
| | | | | 530/418 |
| 2009/0155838 A1* | 6/2009 | Hale | ..................... | A61J 1/2093 |
| | | | | 435/29 |
| 2013/0130401 A1* | 5/2013 | Kanda | ................... | G01N 1/405 |
| | | | | 436/178 |

* cited by examiner

FILTRATION AND EXTRACTION ASSEMBLY

This application claims the benefit of U.S. Provisional Patent Application Ser. No. 61/644,473, filed May 9, 2012; the content of which is hereby incorporated by reference in its entirety.

BACKGROUND

The field of proteomics is an expanding industry which seeks to understand biological systems at the molecular level. Using advanced analytical instrumentation, which includes mass spectrometry (MS) and separation methods such as electrophoresis and liquid chromatography (LC), scientists endeavor to perform a complete characterization of all proteins expressed by an organism. Proteomics has made significant advances in the medical field, establishing a reputation as a leading technology for drug discovery and disease diagnosis. Once considered a tool for chemists, today's analytical instruments are not only more sensitive, but their more robust operation is bringing such platforms to a greater range of end users, including molecular biologists and clinicians.

Proteomics relies heavily on effective and robust sample preparation methods for all steps of analysis to obtain useful quality information. A diverse set of approaches are available to isolate and manipulate proteins ahead of separation (i.e., electrophoresis/LC) and analysis (e.g., MS) to remove the interfering sample components from the protein which may be naturally present in a biological matrix (e.g., lipids, nucleic acids, salts) or are otherwise added to the sample to assist with protein solubilization, preservation, derivatization, or separation (e.g., buffers, detergents, chemical reagents). Techniques such as solvent induced protein precipitation, which use solvents such as acetone or chloroform/methanol to cause the protein sample to form an insoluble pellet, are capable of removing the majority of contaminating species while retaining the protein sample with high recovery. The protocols for solvent precipitation are well established, although they are considered difficult to perform with high reproducibility, requiring a steady hand and considerable patience as they are time consuming to perform for the large sets of samples commonly handled in a proteomics experiments. Even with its drawbacks, solvent precipitation remains a popular method of protein cleanup due to its effective removal of a wide range of contaminates and high recovery of target protein.

No product currently exists to facilitate the cleanup of protein samples by solvent precipitation. The products which are available generally make use of simple membrane filters to purify samples. These remove large particulates from a biological sample (e.g., when using suction filters) but are not capable of meeting all the needs to improving the solvent precipitation protocol. Membranes having permeability to molecules over a specific mass range are available and include simple dialysis membranes and spin-type molecular weight cutoff filers (Millipore's Amicon™ filters). While widely used, these strategies result in lower product yield. Moreover, removing interfering components may be difficult without extensive washing, which results in long processing times.

Numerous products are available for solid phase extraction (SPE). These methods differ from the precipitation method in that the samples are all kept in solution prior to being adsorbed to a solid support; extraction cartridges usually contain SPE material which is selective to a particular group of molecules either by their physical or chemical properties. These materials may be selective for either the proteins, or the contaminants. For example, the ZipTip™ (Millipore) is now a 'classic' approach designed to manipulate small volumes of sample and maintain high protein recovery. Spin filters containing SPE material are also available from various companies which enable SPE to be multiplexed (limited only to the capacity of the centrifuge). Liquid chromatography is a fully automated version of SPE, although this requires expensive instrumentation which becomes tied up in a low-throughput fashion to process samples in series. While high performance liquid chromatography produces a very good purity product and acceptable recovery, this is at high initial instrument cost and a relatively high per-sample time (about 1 hour).

Other methods are available to separate proteins from detergents. These include purification kits available from Pierce, which use selective adsorption of the detergent, and can be used for acceptable purity and relatively fast (10 min) process time. These kits do not separate other impurities, and can have low analyte (protein) recovery. Protein precipitation kits which differ from the standard solvent precipitation methods are available, in which proprietary reagents/solvents are added to cause protein to precipitate. They have acceptable to high recovery, but they require a skilled user and the overall purity is unknown owing to the proprietary reagents involved.

Reviewing the presented methods for the removal of contaminants to generate a pure protein sample with high recovery, there still remains a need for a strategy that can produce purified proteins with broad applicability and with superior purity, recovery, reliability, and speed.

SUMMARY

In general, in an aspect, an assembly for sequential filtration and extraction of a solid is provided, the assembly having a filtration cartridge that is configured to receive, at bottom, an extraction cartridge or a plug, the filtration cartridge having a bottom opening and a membrane covering the bottom opening so as to impede passage of the solid through the filtration cartridge; and an extraction cartridge configured at top to be received by the filtration cartridge, the extraction cartridge having a top opening, a bottom opening configured to receive an extraction cartridge cap, and an extraction cartridge cap; the cap having a central opening large enough to allow elution through the extraction cartridge and small enough to retain SPE materials within the extraction cartridge when it is so charged. Implementations may include one or more of the following features. The filtration cartridge and the extraction cartridge are reversibly attached to each other. The cartridges are substantially cylindrical. The filtration cartridge has an outer wall and the membrane is securely fastened to the outer wall near the bottom opening of the filtration cartridge. The filtration cartridge has a top opening, an outer wall, and protrusions regularly spaced around the outer wall near the top opening. The extraction cartridge is charged with SPE materials.

In general, in an aspect, a filtration cartridge is provided that is configured to receive, at bottom, an extraction cartridge or a plug, the filtration cartridge having a bottom opening and a membrane covering the bottom opening so as to impede passage of the solid through the filtration cartridge.

In general, in an aspect, an extraction cartridge is provided that is configured at top to be received by a filtration cartridge, the extraction cartridge having a top opening, a bottom opening configured to receive an extraction cartridge cap, and an extraction cartridge cap.

In general, in an aspect, a kit is provided that includes a filtration cartridge and an extraction cartridge.

In general, in an aspect, a method of filtration is provided including passing a solution having solvent, soluble contaminants, and solid components of interest through a filtration cartridge of the present invention, such that purified proteins are retained on the membrane.

In general, in an aspect, a method of extraction is provided including solubilizing a precipitated protein and extracting the protein by elution through an extraction cartridge of the present invention. This process may occur within an operating centrifuge.

The present invention concerns, at least in part, a two-stage "filtration and separation/extraction" assembly including a filtration cartridge and an extraction cartridge. The assembly can be disposable. Proteins can be isolated from a variety of interfering components, most notably from ionic detergents, an additive that is generally necessary yet very difficult to eliminate. Within the first (filtration or preparation) stage, proteins are captured in the filtration cartridge using a modified organic solvent precipitation protocol, being retained on a membrane support while allowing interfering components to be removed. During this stage, the filtration cartridge acts as a classic reaction vessel (e.g., a test tube or vial), allowing for the solvent precipitation to be carried out without risk of sample loss. In the second (extraction or collection) stage, proteins retained as a solid precipitate are recovered through stepwise solubilization, extraction and elution from an extraction cartridge containing SPE. By allowing the combination of protein precipitation chemistry, filtration, and SPE into a single technique, this technology not only delivers simplicity of use (the cartridge can also be disposable), a higher degree of throughput, and a large range of applications, but equally important it offers a cost-effective means for large scale sample preparation.

The present invention in its various aspects may have any of the following advantages. Process time can be short compared to current procedures (e.g., approximately 5 to 15 minutes vs. 1-2 hours with conventional procedures). The quality and reliability of the sample purification protocol are enhanced over conventional precipitation protocols, which require a trained user to isolate the precipitate from the residual solvents. In disposable embodiments, the risk of sample carryover is eliminated, ensuring the quality and reliability of each sample being processed. Analyte recovery is excellent (approaching 100%), and purity of the product produced is generally superior to all protein purification strategies in the prior art. Salts and detergents are removed from the protein because such compounds remain in solution during the centrifugation process while the protein, in pellet form, is retained by the membrane filter.

These and other features and aspects, and combinations of them, may be expressed as methods, systems, components, means and steps for performing functions, business methods, program products, and in other ways.

Other advantages and features will become apparent from the following description and from the claims.

DESCRIPTION

Figure 1:
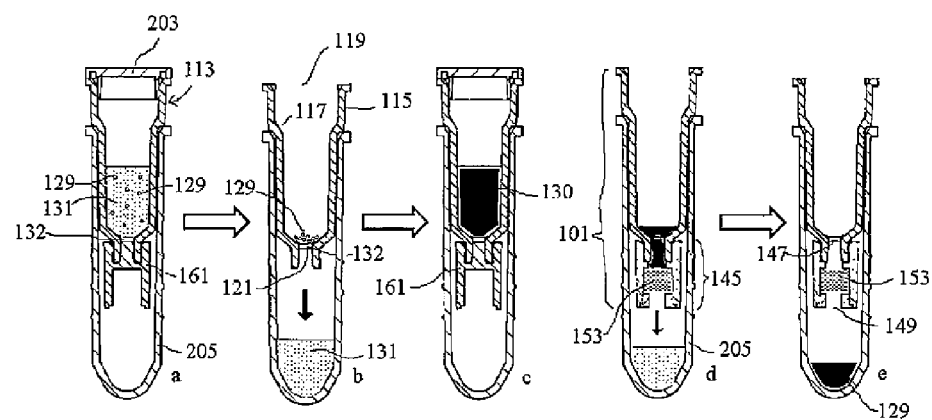
FIG. 1 illustrates the process of using an embodiment of a two-stage filtration and extraction assembly by section view.

FIGS. 11 through 22 supply further information about experimental details in methods of the present invention, as well as comparison to methods known in the art.

PARTS LEGEND

101 Filtration and extraction assembly
103 First stage
105 Second stage
107 Top of the assembly
109 Middle of the assembly
111 Bottom of the assembly
113 Filtration cartridge
115 Outer wall of the filtration cartridge
117 Inner wall of the filtration cartridge
119 Top (opening) of the filtration cartridge
121 Bottom (opening) of the filtration cartridge
123 Circular extension
125 Protrusion
127 Samples
129 Solid components of interest, analyte
130 Solvent containing resolubilized precipitate
131 Solvent and soluble contaminants
132 Membrane
133 Coupling ring
145 Extraction cartridge
147 Top opening of the extraction cartridge
149 Bottom opening of the extraction cartridge
151 Interior of extraction cartridge
153 SPE materials
155 (Bottom of the) extraction cartridge cap
157 Central opening of the extraction cartridge cap
161 Plug
201 Void volume
203 Cover
205 Centrifuge tube

DEFINITIONS

By quality or purity, we are describing an objective, which is to remove contaminants to make the solid components of interest as homogeneous or pure as possible. In some embodiments, the solid components of interest are proteins. In other embodiments the solid components are DNA or RNA or lipid materials. Still in other embodiments, the solid components are small molecules, such as drugs or metabolites. In some embodiment, the contaminants represent all portions of the sample other than the analyte and the solvent (water or other). These may include salts, buffers, detergents, or other components which are naturally found in the sample or are added to the sample by the user during other sample manipulation steps. In some embodiments, the sample contains proteins being processed prior to mass spectrometry analysis. By yield or recovery, we are describing an objective, which is to keep as much of the solid components of interest as possible. By reliability, we mean that use of the assembly or its components in the methods of the present invention produce results which are highly reproducible. By throughput, we refer to the speed at which a single sample can be processed, or the ability to process multiple samples in parallel, while still maintaining a relatively rapid processing time. By ease of use, we are referring to the ability to maintain all desired aspects of the manipulation (recovery, purity, reliability, throughput) with minimal training, or with minimal attention being placed on the operations involved in the sample processing.

A two-stage filtration and extraction assembly is disclosed herein which enhances the effectiveness (e.g., the percentage of protein recovered, the purity of the analyte), reproducibility, and throughput of conventional protein precipitation protocols. The assembly is usable in a number of environments. In some embodiments, the assembly is disposable, or fabricated of disposable material such as injection molded plastic.

Use of the assembly 101 can be seen with reference to letters in FIG. 1. Precipitation occurs directly within the upper portion of a filtration cartridge (113 at a). A membrane 132 at the bottom/base 121 of the filtration cartridge permits capture of solid components of interest 129 within the upper portion of the cartridge, with removal of solvent and soluble/dissolved contaminants 131 proceeding by gravity filtration or by spinning the cartridge in a centrifuge (b). Following resolubilization of the precipitate 130 (c), an extraction cartridge 145 enables solid phase extraction (SPE) through a series of simple spins inside the centrifuge (d-e).

When preparing for filtration through a filtration cartridge 113 without an extraction cartridge 145 attached, a plug 161 that blocks all fluid flow out of the cartridge may be added to the bottom 121, in order to keep filtration from occurring. This plug has a radius similar to that of the top of the extraction cartridge 147, is solid, and may have a extension of radius smaller than the bottom 121 of the filtration cartridge 113 that extends as high as the membrane 132 inside the filtration cartridge 113 (in such embodiments, the membrane can be supported by the plug). The 'fit' of the plug may be slightly more 'tight' (i.e., a harder snap fit) than the extraction cartridge, in order to ensure a water tight seal, even when found inside an operating centrifuge. This can be done by adjusting the dimensions of the plug relative to the bottom (i.e., the base) of the filtration cartridge 121. The plug can also be used for storage of samples of interest for longer term, e.g., a period of time covering several days or several months, up to periods of time covering several years.

Figure 2:
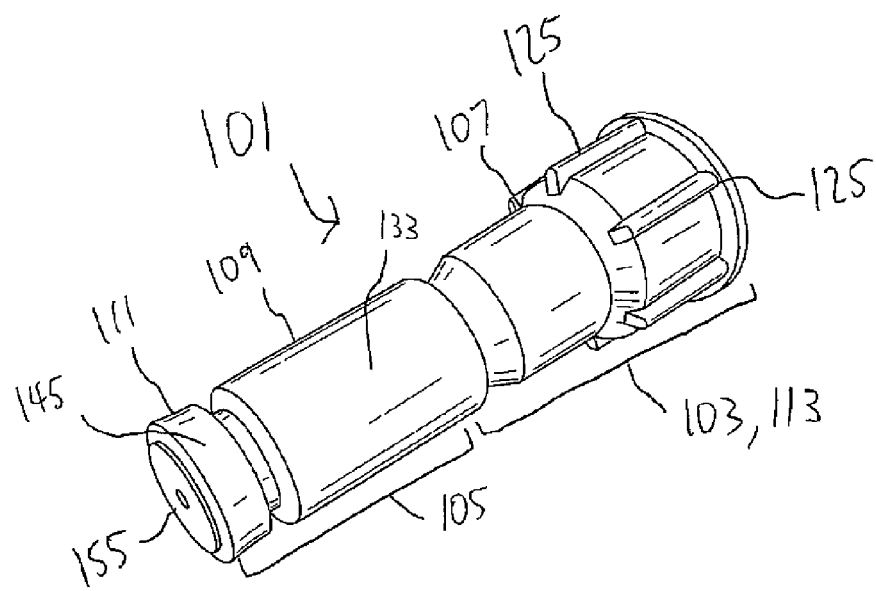
FIG. 2 shows a perspective view of a filtration and extraction assembly featuring a coupling ring.
Figure 3:
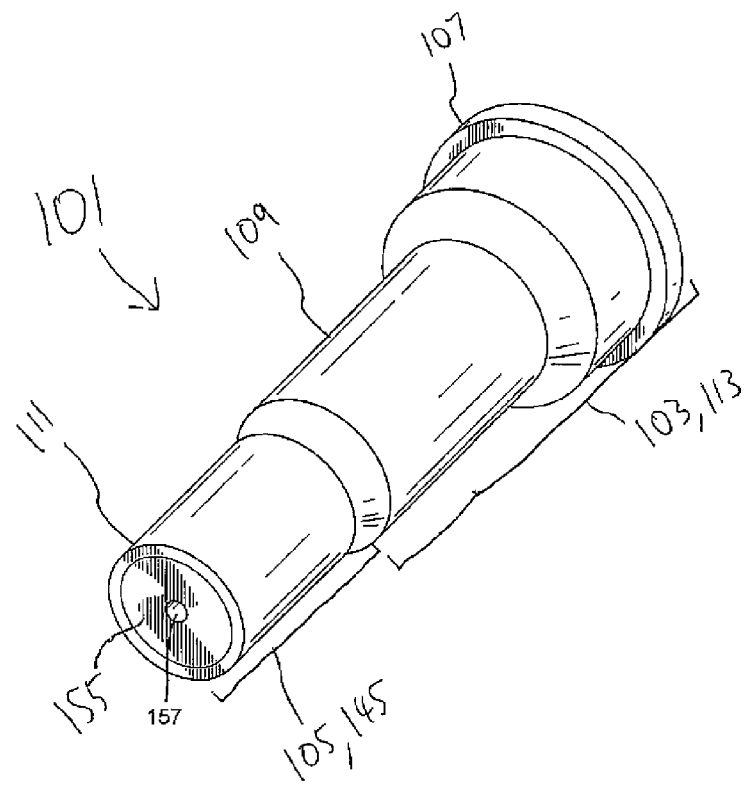
FIG. 3 shows a perspective view of a filtration and extraction assembly not featuring a coupling ring.
Figure 4:
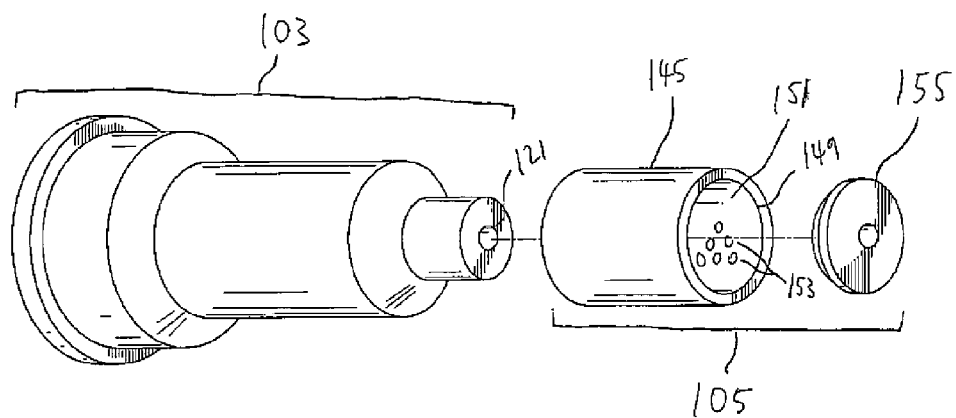
FIG. 4 shows an exploded view of a filtration and extraction assembly.

In some embodiments, such as that illustrated in FIG. 2 or in sectional view at FIG. 1, in the first stage 103 at the top of the assembly 107, there is a substantially cylindrical filtration cartridge 113 having an outer wall 115 and an inner wall 117. The filtration cartridge has a height greater than its radius and has openings on top 119 and bottom 121 through which material may pass. In some embodiments, the radius of the cartridge decreases near the bottom such that it tapers. In some embodiments, the outer wall near the top of the filtration cartridge has protrusions 125 of a size sufficient to prevent the assembly from falling into a centrifuge tube 205 during active centrifugation. In some embodiments, the protrusions 125 are fin-shaped and regularly spaced around the outer wall. Use of this embodiment is as follows. At initial charging, samples 127 containing liquid (solvent) and soluble contaminants 131 as well as the analyte/solid components of interest 129 are added to the filtration cartridge through the top opening. Reagents or solvents are added through the top 119 of the upper filtration cartridge, thus inducing the analyte to precipitate from solution, forming solid components of interest 129. In some embodiments, a membrane 132 is attached to several points around the wall near the bottom 121 of the filtration cartridge 113, such that the membrane 132 spans the bottom opening and impedes passage of solid components of interest 129. In some embodiments, such as that according to FIG. 2, in the first stage 103 in the middle 109 of the assembly 101, there is also a substantially cylindrical coupling ring 133 having a top opening and a bottom opening, with a height greater than its radius and of a radius larger than that of the filtration cartridge radius, such that the bottom of the filtration cartridge can be snugly placed inside the coupling ring 133 through its top opening. In some embodiments, the height of the coupling ring 133 is sufficient to also snugly place a extraction cartridge 145, described below, inside the ring through the bottom opening. At approximately the midpoint of the ring, there is a circular wall having a central opening of a radius sufficient to allow at least a part of a sample to pass through the ring from top to bottom. In some embodiments, the surface of the circular wall which is facing the top opening of the ring has a membrane spanning the central opening and impeding passage of the solid components of interest. In some embodiments, in the second stage 105 at the bottom 111 of the assembly 101 is a substantially cylindrical extraction cartridge, partially enclosed on the top, that has a bottom opening; the cartridge also has a top opening of radius similar to that of the central opening of the coupling ring that is configured to be received by the coupling ring.

In some embodiments, the extraction cartridge 145 is filled with materials useful for solid phase extraction (SPE materials 153). These may include reversed phase materials including bonded phase silica (ie C4, C8 or C18 packing material) or polymeric polymer particles which present a hydrophobic support phase, ion exchange resins which include positive or negatively charged surfaces, gel filtration material which comprises particles with pores of a given size to facilitate retention of analytes over a given radius or molecular weight, affinity based support, including surfaces which are designed to bind metals to be used in metal affinity chromatography, or antibody based capture materials, or any similar packing material used in high performance liquid chromatography. The dimensions of the particles (particle diameters) may be of a size similar to liquid chromatography, or may be slightly larger, allowing control of the force required to move solvent through said packing material. In some embodiments, an extraction cartridge cap 155, having a central opening 157 of radius similar to that of the top opening 147 of the extraction cartridge 145 and which runs approximately the full height of the cap, holds the SPE materials 153 in place while allowing for passage of the solid components of interest. In other embodiments, the packing material includes a single continuous phase (monolithic support), which also acts to retain analytes or to isolate contaminants from the analytes by selectively retaining either the analyte or non analyte sample components. The second stage 105 can be used to perform conventional SPE in the absence of the first stage 103. In preferred embodiments, the second stage 105 follows the first stage 103; use of the second stage of the present invention in a centrifuge is described in the Examples and generally comprises the steps of resolubilizing the solid components of interest in the filtration cartridge 113, placing the assembly 101 into a centrifuge tube 205 of suitable dimensions, and running the centrifuge at such speed and time as is necessary to pull the solid components of interest through the filtration cartridge and extraction cartridge, resulting in high purity solid components of interest in the centrifuge tube. In some embodiments, the process can be fully automated by preloading a plurality of cartridges into a centrifuge properly equipped with the appropriate sample ports. Note that elution of the solid components of interest may take place following solubilization of said solid components to form a suspension of finer particles, or in a preferred embodiment, to dissolve such solid components into solution using an appropriate solvent; recovery of the high purity (once solid) components of interest 129 may proceed by first passing the samples through the extraction cartridge 145, recovering such components through methods which are generally known in the art. In some embodiments, recovery of analyte may proceed without passing the sample through the extraction cartridge 145. Analytes may be passed through the filtration cartridge 113 and collected into a centrifuge vial 205, or they may even be transferred through decanting or pipetting the analyte from the top of the filtration cartridge 113. In some embodiments, the solid components of interest 129 are to remain suspended in any liquid eluted. In other embodiments, the liquid is removed through evaporation.

Suitable materials for membranes in filtration cartridges of the present invention include filter paper, scintered glass disks, glass membrane filters, PTFE filters or other membranes of defined (e.g., molecular weight cutoff filters) or approximately defined (according to size, e.g., 0.2 micron, 2 micron, 20 micron, etc.) porosity. In an embodiment, the membrane is fabricated of polytetrafluoroethylene (PTFE) and is of approximately 0.45 microns in porosity (pore size). In an embodiment, the membrane is fabricated of PTFE and is of approximately 0.2 microns in porosity. The porosity of the membrane can be selected so as to restrict or slow down the flow of solvent through the membrane, which may result in better filtration or in minimization of solvent accidentally dripping through the cartridge at times when the cartridge it is not properly placed for collection of the liquid. In some embodiments utilized for filtering samples containing aqueous liquid, the membrane is composed chiefly of hydrophobic materials. Both the pore size as well as the chemical composition of the filter play a role in restricting the flow of solvent.

In embodiments having no membrane or when samples are dissolved in solution, samples pass through the first stage 103 generally unimpeded. In preferred embodiments, there is at least one membrane and solid components of interest 129 remain in the filtration cartridge 113 after the solvent and soluble contaminants 131 have been substantially removed. In some embodiments, gravity filtration is sufficient to remove the liquid and soluble contaminants; in some embodiments, centrifugation is desired to remove the liquid and soluble contaminants. Use of the first stage 103 of the present invention in a centrifuge is described in the Examples and generally comprises the steps of initially charging the filtration cartridge, placing at least the filtration cartridge into a centrifuge tube of a radius slightly larger than the first stage and a height at least as great as the piece inserted, and running the centrifuge at such speed and time as is necessary to substantially remove liquid and soluble contaminants 131 from the filtration cartridge.

In embodiments where the membrane is attached directly to the filtration cartridge, such as that illustrated in FIGS. 3, 4, and 7-11, it is not necessary to include a coupling ring. In embodiments where the membrane is attached to a coupling ring, the entire first stage may be inserted into the centrifuge. In some embodiments, the first stage 103 is connected to the second stage 105 and the entire filtration and extraction assembly is placed in the centrifuge tube. In some embodiments, the process can be fully automated by preloading a plurality of cartridges into a centrifuge properly equipped with the appropriate sample ports. In embodiments where the filtration cartridge bottom 121 is adapted to receive the top 147 of an extraction cartridge 145, the two cartridges can be reversibly attached. In some such embodiments, a circular extension 123 from the bottom 121 of the filtration cartridge 113 is of slightly smaller radius than the top opening 147 of the extraction cartridge 145, allowing for the cartridges to "snap" together. The snugness of this fit is generally enough to allow the user to remove the extraction cartridge from the filtration cartridge by hand, or with minimal effort (e.g., with the aid of a grasping tool). The fit is also intended to keep the two cartridge firmly attached to each other, forming a water tight seal that is maintained even during centrifugation. In some embodiments, the seal is accomplished using rubber rings around the circular extension. In other embodiments, the seal may be maintained by machining a screw pattern on the circular extension and the inner wall of the top opening 147, such that they would screw together.

Manufacture of the assembly 101 of FIGS. 3, 4, and 7-11 can proceed by injection molding, followed by insertion of an appropriate membrane through the top of the assembly and attachment (by heat, adhesion, or other methods known in the art) of the membrane to the assembly such that it is securely fastened, spans the opening at bottom 121, and impedes passage of the solid components of interest 129.

Figure 5:
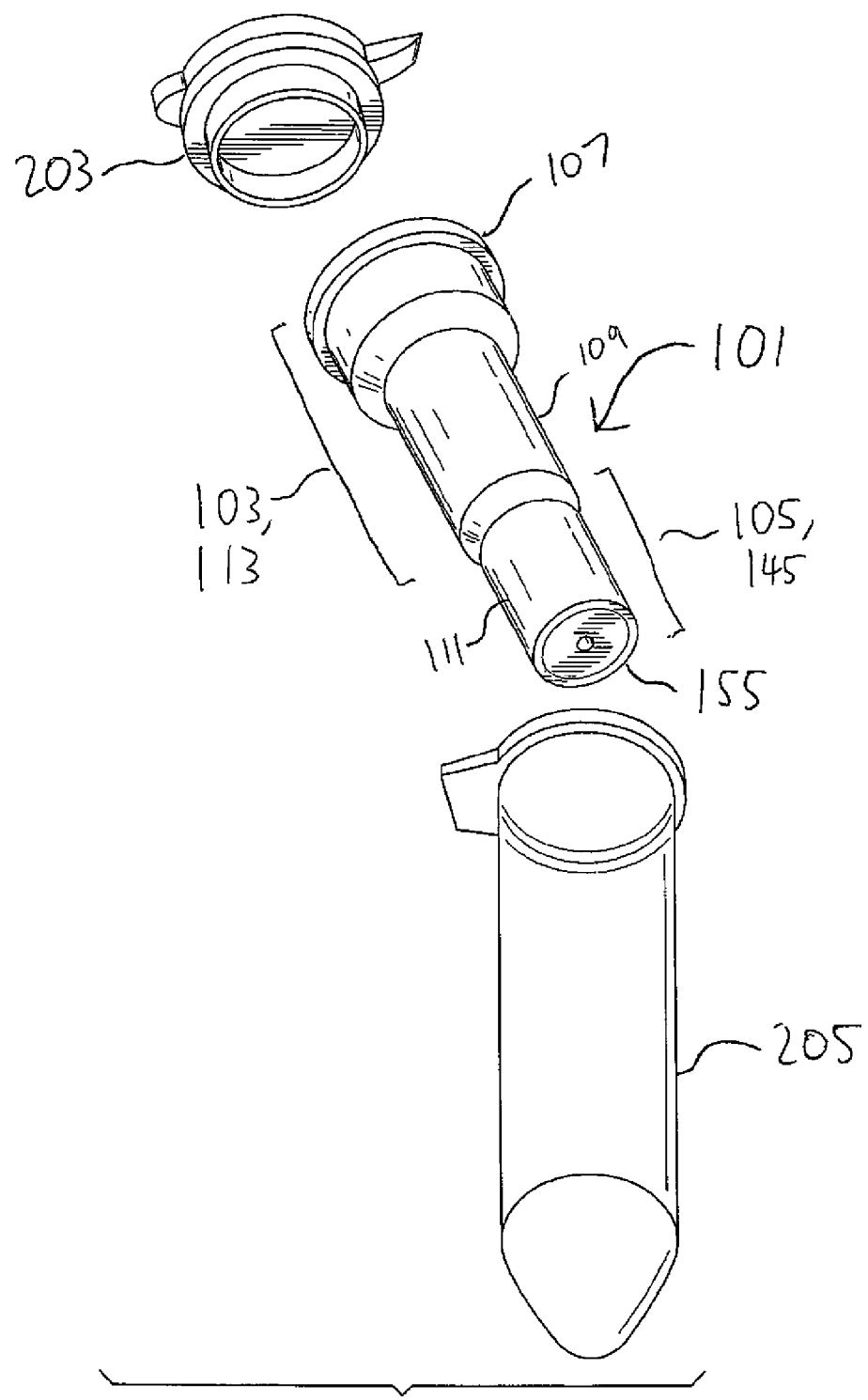
FIG. 5 shows an exploded view of a filtration and extraction assembly in a use environment.
Figure 6:
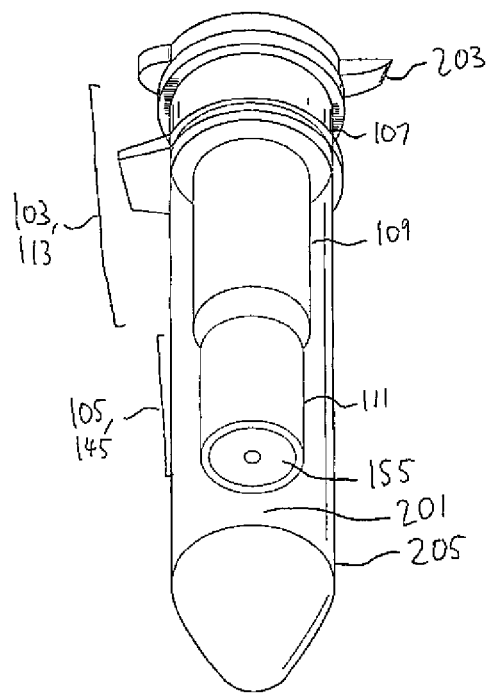
FIG. 6 shows a filtration and extraction assembly in a use environment (e.g., a centrifuge tube).
Figure 7:
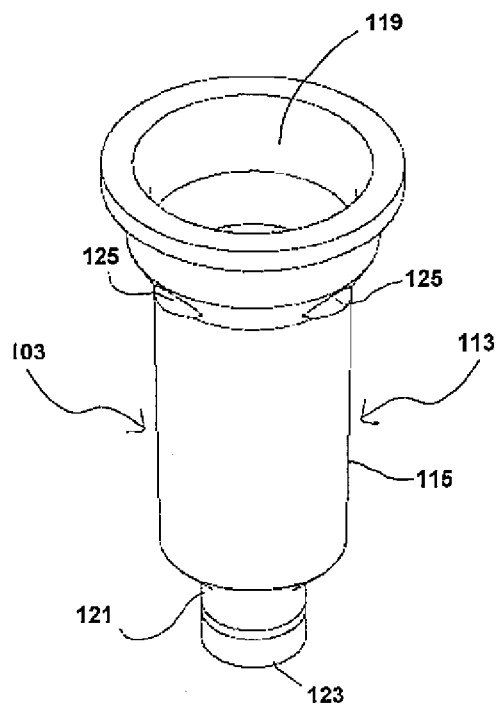
FIG. 7 shows a side view of a filtration cartridge (top shown)
Figure 8:
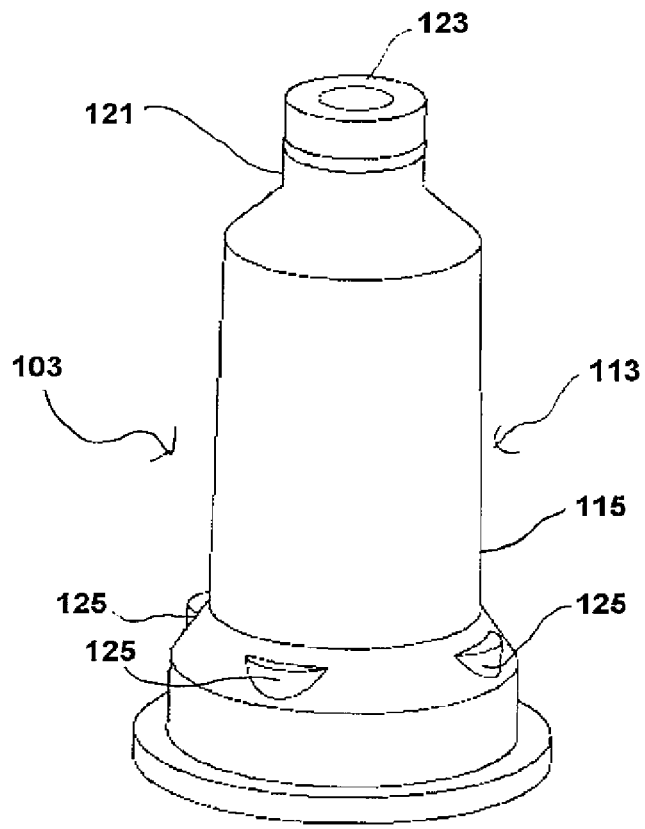
FIG. 8 shows a side view of a filtration cartridge (base shown)
Figure 9:
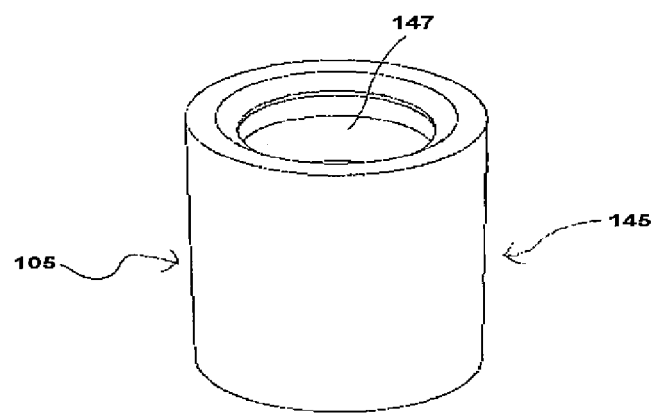
FIG. 9 shows a side view of an extraction cartridge (top shown)
Figure 10:
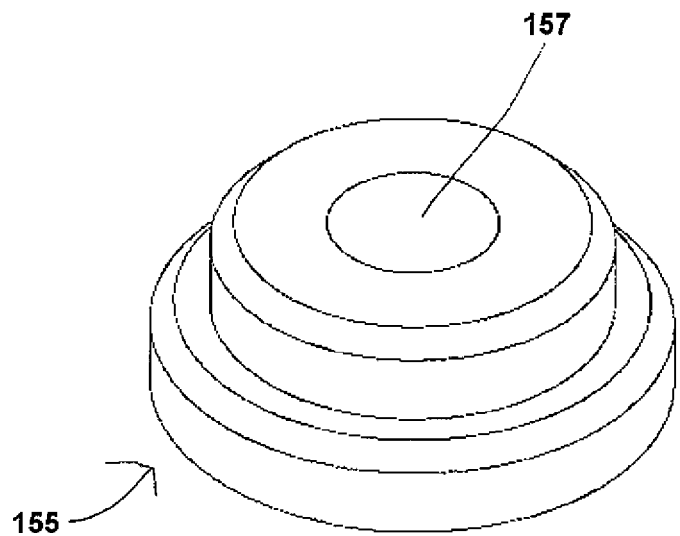
FIG. 10 shows a side view of an extraction cartridge cap.

In some embodiments, the assembly 101 is sized to fit into the sample ports on a benchtop micro centrifuge or into the vials or tubes 205 generally used in such centrifuges. Appropriate form factors for the assembly generally overhang the top of a tube or vial, or otherwise provide means such that they do not fall into the tube or vial; such sizing also generally allows for the bottom of the assembly 111 to lie within the tube or vial, leaving void volume 201 below the bottom of the extraction cartridge 145 in which to capture solvent (which in some cases may be contaminant, in others the analyte or sample, depending on the solvent system and SPE materials used). Examples of appropriate tubes or vials include standard centrifuge tubes, small minicentrifuge tubes of approximate volume from 0.6 to 1.6 mL, 15 mL Falcon tubes, and 50 mL falcon tubes. Airflow is maintained as liquid moves through the stage so as to avoid making an airtight seal. This can be accomplished in a number of ways, including providing a series of holes spaced around the top of the assembly (not shown) or leaving a large enough gap between the top of the assembly 107 and the centrifuge tube 205 to prevent a vacuum from forming. In some configurations, a cover 203 is placed inside or upon the top of the assembly 107. See FIGS. 5 and 6 for illustrations of a relevant embodiment.

In some embodiments, a two stage filtration and extraction assembly comprises a disposable filtration cartridge and a disposable extraction cartridge. In some embodiments, the assembly fits within a standard 2 mL vial. In some embodiments, the filtration cartridge is approximately 500 μL in volume and is equipped at its base with a membrane, the membrane being fabricated of polytetrafluoroethylene (PTFE) and being approximately 0.45 μm in porosity. In some embodiments, a cap attaches to the top of the filtration cartridge. In some embodiments, the extraction cartridge contains polymeric reverse phase SPE materials. In some embodiments, a filtration cartridge has flow of solvent blocked by way of a plug.

In some embodiments, a two-stage assembly, or one of the two stages, may be used within a microcentrifuge tube which is in turn placed inside a benchtop microcentrifuge. Optimal speed of operation within such a microcentrifuge may vary depending on the type of material to be filtered or extracted, and on whether both stages or only one stage (possibly also including a plug) are being used. In some embodiments utilizing one stage with a plug, the maximum effective operating speed is approximately 7,500 RPM (5,400×G). In some two-stage embodiments, the maximum effective operating speed is approximately 6,000 RPM (3,500×G). Generally, for samples containing aqueous liquid, the centrifuge speed may be higher than for samples containing other liquids.

EXAMPLES

The following are example methods of the present invention; many other methods are also possible. For methods utilizing a centrifuge, if liquid remains in filtration cartridge, then return it to the centrifuge and repeat the spin cycle. Spin speed and times are guidelines only; unless otherwise indicated, no cap should be present during spin, and the centrifuge should be balanced by placing an assembly of roughly equivalent mass opposite the assembly of interest. For methods utilizing filtration, if the plug or SPE cartridge is to be removed and solvent is present in the filtration cartridge, then the cap should be attached to the top of the filtration cartridge and the assembly inverted. Precipitation efficiency of protein recovery in applicable methods of the invention may exceed 95 percent and SPE column recovery may exceed 95 percent, as determined through a commercial Pierce BCA assay (ThermoFisher Scientific), using from 1 to 30 µg protein standard (bovine serum albumin or a proteome mixture from $E.$ $coli$. SDS removal in applicable methods of the invention may exceed 99 percent, as measured by the methylene blue spectroscopic assay (for an abbreviated protocol, see Arand et al, Anal. Biochem., 1992, 207, p 73-75; hereby incorporated by reference).

Example 1

Protein Precipitation with Acetone

The plug is attached to the base of the filtration cartridge and the device is placed into a standard 1.5 mL micro centrifuge tube. Into the filtration chamber, 100 µL of solution containing 1 to 100 µg of protein is added. Solvent precipitation is performed by addition of 400 µL cold acetone. The device is capped and incubated overnight at −20° C. The device is then centrifuged for 1-10 min to form a pellet at the bottom of the filtration chamber. Next, the cover and plug is removed and the solvent (containing the unwanted impurities) is passed through during centrifugation, retaining the protein sample in pellet form. The pellet is washed by addition of 400 µL cold acetone followed by centrifugation to remove nearly all unwanted contaminants, and the wash step is optionally repeated. The wash solutions are discarded. Next, the extraction cartridge containing SPE materials is attached to the filtration cartridge and placed into a fresh microcentrifuge tube. The protein pellet is solubilized using 10 to 100 µL of appropriate solvent (eg 8 M urea, 90% formic acid, or 0.5% ammonium perfluorooctanoate in water) then passed onto and bound to the SPE during centrifugation at low speed (~20×g). The flow through and vial are discarded and the device is placed into a fresh vial. The protein is then eluted from the SPE during centrifugation using appropriate solvents (eg 50% acetonitrile, 0.1% formic acid, for a reversed phase cartridge) and collected into the vial for further analysis.

Example 2

Protein Precipitate by 2 Step Chloroform, Methanol, Water

The plug is attached and the device is placed into a standard 1.5 mL plastic vial. Into the filtration cartridge 100 µL of solution containing 1 to 100 µg of protein is added. Solvent precipitation is performed by addition of 400 µL methanol, 100 µL chloroform, and 300 µL water. The cover is attached and the device is centrifuged for 15 minutes at ~20,000×g to form the protein pellet. In step 2, the plug and cover are removed and the solvent (containing the unwanted impurities) is passed through to waste during centrifugation, retaining the protein sample in pellet form. The pellet is washed twice by addition of 400 µL methanol followed by centrifugation and the vial and wash are discarded. In step 3, the extraction cartridge containing SPE materials attachment is placed onto the device. The protein pellet is solubilized using an appropriate solvent then passed onto and bound onto the SPE during centrifugation. The protein is then be eluted from the SPE using appropriate solvents and collected for further analysis.

Example 3

Precipitate, Resolubilize, Trypsin Digest in Filtration Cartridge (Upper Vial), then SPE The plug is first attached and the device is placed into a standard 1.5 mL plastic vial. Into the filtration cartridge 100 µL of solution containing 1 to 100 µg of protein is added. Either acetone or chloroform/methanol/water precipitation is performed as described in examples 1 and 2. In step 2, the plug and cover are removed and the solvent is passed through to waste during centrifugation, retaining the protein sample in pellet form. The pellet is washed twice by addition of 400 µL acetone/methanol followed by centrifugation, the wash and vial are discarded and the device is placed into a fresh vial. In step 3, the plug is reattached and the pellet is suspended into 100 µL of either 100 mM Tris-HCl or 100 mM ammonium bicarbonate buffer at pH 8.0 in water. The protein may optionally be reduced and alkylated prior to enzymatic digestion, which involves the addition of 100 ng to 1 µg trypsin (or other suitable protease enzyme). The cover is attached and the sample is incubated for 4 to 24 hours at 37° C. Following incubation, the cover is removed and the solution is acidified with addition of 10 µL 10% trifluoroacetic acid or formic acid. In step 4, the plug is removed and replaced with the extraction cartridge containing SPE materials. The digested protein in solution is passed onto and bound to the SPE by centrifugation. Appropriate solvent is then used to elute the sample from the extraction cartridge containing SPE materials into the vial for further analysis.

Example 4

Precipitate, Resolubilize, Trypsin Digest (without SPE)

The plug is first attached and the device is placed into a standard 1.5 mL plastic vial. Into the filtration cartridge 100

µL of solution containing 1 to 100 µg of protein is added. Either acetone or chloroform/methanol/water precipitation is performed as described in examples 1 and 2. In step 2, the cover and plug is removed and the solvent is passed through to waste during centrifugation, retaining the protein sample in pellet form. The pellet is washed twice by addition of 400 µL acetone/methanol followed by centrifugation and the wash and vial is discarded, the device is placed into a fresh vial. In step 3, the plug is reattached and the pellet is suspended into 100 µL of either 100 mM Tris-HCl or 100 mM ammonium bicarbonate buffer at pH 8.0 in water. The protein may then be reduced and alkylated prior to enzymatic digestion with the addition of 100 ng to 1 µg trypsin (or any other protease enzyme). The cover is attached and the sample is incubated for 4 to 24 hours at 37° C. Following incubation, the cover is removed and the solution is acidified with addition of 10 µL 10% trifluoroacetic acid or formic acid. In step 4, the plug is removed and the sample in solution is spun out into a collection vial for further analysis. Alternatively, the plug can remain and the device used as an autosampler vial for liquid chromatography.

Example 5

SPE without Precipitation, Using Filtration Cartridge as a Means of Filtering Non-Dissolved Particles The extraction cartridge containing SPE materials attachment is first connected to the device then placed into a standard 1.5 mL plastic vial. Sample is added to the filtration cartridge and the device and spun in a centrifuge at low speed, filtering out particulate matter while allowing sample to bind to the extraction cartridge containing SPE materials. Non-binding compounds in the solvent are collected into the vial and can be either discarded or kept for further analysis. An optional washing step can be including by adding the washing solvent to the upper cartridge, then slowly spinning the cartridge in a centrifuge which allows the solvent to pass through the extraction cartridge containing SPE materials. The wash solvent is collected in the microcentrifuge tube and discarded. The device is then placed into a fresh 1.5 mL vial and appropriate eluting solvent is added to the filtration cartridge, followed by centrifugation to elute and collect the sample from the extraction cartridge containing SPE materials.

Example 6

Filtration, as Used to Clarify the Sample of Solid Particulates

The device is placed into a standard 1.5 mL plastic vial without the plug or SPE attachments. The sample solution is placed into the filtration cartridge. The device undergoes centrifugation and the sample is collected into the vial while particulate matter is retained on the membrane filter. The clarified sample can then be frozen or used for further analysis.

Example 7

Precipitate Protein, then Filter Out Using Upper Cartridge, where the Analyte Constitutes the Non-Protein Materials (e.g., for Drug/Metabolite Work)

The plug is first attached and the device is placed into a standard 1.5 mL plastic vial. Into the filtration cartridge, 100 µL of sample is added. Either acetone or chloroform/methanol/water precipitation is performed as described in examples 1 and 2. In step 2, the cover and plug is removed, the device is centrifuged and the sample solution containing the analytes of interest (non-protein) is collected into the plastic vial for further analysis. Protein in pellet form is retained on the filter and discarded with the device.

Example 8

Using Filtration Cartridge as a 'Storage Container' for Precipitated Materials, or for Solids that have been Isolated from the Sample The plug is first attached and the device is placed into a standard 1.5 mL plastic vial. Into the filtration cartridge 100 µL of solution containing 1 to 100 µg of protein is added. Either acetone or chlorofrom/methanol/water precipitation is performed as described in examples 1 and 2. In step 2, the cover and plug is removed and the solvent is passed through to waste during centrifugation, retaining the protein sample in pellet form on the membrane filter. The pellet is washed twice by addition of 400 µL acetone/methanol followed by centrifugation. The wash and vial are discarded and the device is placed into a fresh vial. The plug and cover are attached and the device is placed into frozen storage until further analysis.

Example 9

Protein Purification in Acetone

A plug was attached to the base of a filtration cartridge containing a PTFE filter. 100 uL of protein-containing sample was added to the filtration cartridge. 400 uL of acetone at approx. −20 degrees C. was then added, and the cap was placed on the cartridge. The cartridge was inverted and then inserted into a 2 mL vial, followed by incubation of the assembly overnight at approx. −20 degrees C. The assembly was then centrifuged at approximately 5,500 RPM for approx. 5 minutes, resulting in precipitated protein adhering to the polyfluorotetraethylene membrane of the cartridge. The assembly was inverted and then plug removed. The now-unplugged assembly was centrifuged at approx. 2,000 RPM for approx. 1 minute, resulting in solvent and sample being displaced from the cap. The cap was then removed and the cartridge was centrifuged at approx. 2,000 RPM for approx. 5 minutes in the vial. The liquid in the vial was discarded. For improved analyte purity, 400 uL of acetone at −20 C. was added to the cartridge and it was again centrifuged for approx. 2,000 RPM for approx. 5 minutes. The protein was therefore in an intact and purified state.

Example 10

Protein Precipitation in Chloroform, Methanol, Water

A plug was attached to the base of a filtration cartridge containing a PTFE filter. 200 microliters of methanol and 50 microliters of chloroform were added to the filtration cartridge. A cap was placed on the top of the filtration cartridge and then the capped and plugged cartridge was vortexed for approximately 5 seconds to combine the solvents. The cap was removed. 50 microliters of protein-containing sample were added to the filtration cartridge, the cap was attached again, and it was again vortexed briefly. The cap was removed, 150 microliters of water was added, and the cap was attached again. The cartridge was then inverted twice to gently mix the contents, followed by centrifugation in a 2 mL vial at approximately 5,500 RPM for approximately 5 minutes. The cartridge was inverted, the plug was removed, and then it was placed back into the vial and the centrifuge. Centrifugation at approx. 2,500 RPM for approx. 5 minutes resulted in flow-through of solvent. The cap was then removed and the cartridge again centrifuged in the vial for an additional 1 minute at approx. 2,500 RPM. An optional washing step was then performed: 200 microliters of acetone were added to the top of the filtration cartridge and the cartridge was centrifuged in the vial at approx. 2,000 RPM. The protein remaining in the filtration cartridge was air dried in a fume hood.

Example 11

Resolubilization of Protein

Once intact protein has been obtained in a filtration cartridge (for example, by following steps described in examples 9 or 10), resolubilization is possible as follows. A plug was attached to the base of the filtration cartridge. 100 microliters of 80% formic acid/20% water was added to the top of the filtration cartridge. A cap was placed on top of the cartridge, and the capped and plugged cartridge was then vortexed for 1 minute. The cap was removed, and 400 microliters of water were added. The cartridge was again capped, and it was inverted twice in order to mix the solvents. Recovery of protein is possible by removing the plug and centrifuging in a 2 mL vial at approx. 2,000 RPM for approx. 5 minutes.

Example 12

Digestion of Protein

Once intact protein has been obtained in a filtration cartridge (for example, by following steps described in examples 9 or 10), digestion is possible as follows. A plug was attached to the base of the filtration cartridge. 50 microliters of 8 M urea was then added. A cap was placed on top of the cartridge, and the capped and plugged cartridge was vortex for approx. 1 minute. The cartridge was set aside at room temperature for approx. 30 minutes. Then, the cap was removed and 200 microliters of 100 mM Tris buffer (pH 8) was added to the top of the filtration cartridge.

The cap was replaced and the cartridge vortex briefly to combine the solvents. An optional reducing/alkylating step was performed by removing the cap and adding DTT (final 9.5 mM), then iodoacetamide (final 19 mM), letting stand for approx. 1 hour after each chemical addition. Trypsin was then added at a mass equal to approximately 50:1 trypsin: protein. The cartridge was capped and incubated in a 37 degree C. water bath for at least one hour (can be overnight). The digestion was stopped by uncapping the cartridge and adding trifluoroacetic acid to a final volume concentration of 1%. Digested protein (i.e., peptides) may be recovered by removing the plug and centrifuging the cartridge in a 2 mL vial at approx. 4,000 RPM for approx. 5 minutes.

Example 13

Protein or Peptide Cleanup Using Extraction Cartridge

Recovery of protein or peptide in Examples 11 or 12 can be accomplished as described in those Examples, or if cleanup is desired, by the steps of this Example.

Prime: An extraction cartridge containing SPE was attached to the base of a clean (i.e., a priming) filtration cartridge. 300 microliters of acetonitrile were added to the top of the filtration cartridge. The assembly was placed in a 2 mL vial and centrifuged for approx. 3,000 RPM for approx. 3 minutes. 300 microliters of trifluoroacetic acid 0.1% aqueous solution were added to the top of the filtration cartridge and centrifugation was performed at 4,500 RPM for 5 minutes. The extraction cartridge was then primed.

Load and wash: The extraction cartridge was attached to the base of a protein- or peptide-containing filtration cartridge. If a protein as in Example 11, the assembly was centrifuged in a 2 mL vial for approx. 3,500 RPM for approx. 5 minutes; if a peptide as in Example 12, the assembly was centrifuged in a 2 mL vial for approx. 4,500 RPM for approx. 5 minutes. The solvent in the vial was discarded. 300 microliters of 0.1% TFA aqueous/5% isopropanol were added to the top of the filtration assembly. The assembly was centrifuged in a 2 mL vial for approx. 4,500 RPM for approx. 5 minutes. The solvent in the vial was discarded.

Elution: If a protein as in Example 11, 300 microliters of 30% isopropanol/49% formic acid/21% water were added to the top of the filtration cartridge; the assembly was then centrifuged in a 2 mL vial at approx. 3,000 RPM for approx. 5 minutes. 300 microliters of 40% isopropanol/42% formic acid/18% water were then added to the top of the filtration cartridge; the assembly was centrifuged in the vial at approx. 3,000 RPM for approx. 5 minutes, resulting in eluent in the vial. This elution step was repeated as necessary, pooling the eluent. If a peptide as in Example 12, 300 microliters of 50% acetonitrile/0.1% trifluoroacetic acid aqueous were added to the top of the filtration cartridge; the assembly was then centrifuged in a 2 mL vial for approx. 3,000 RPM for approx. 5 minutes, resulting in eluent in the vial, repeating and pooling eluent as necessary.

Data

Example 14

Measure of Protein Recovery

Figure 11:
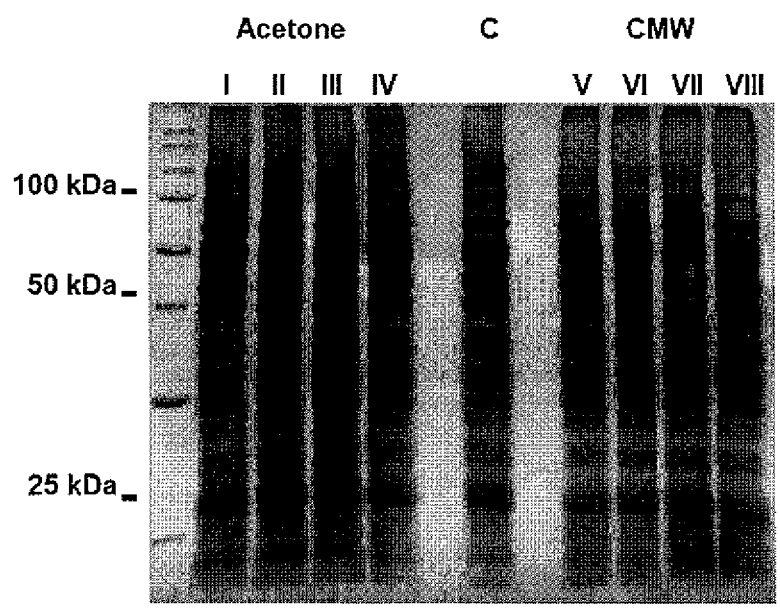

FIG. 11 shows a one dimensional SDS-PAGE silver stained gel image, displaying protein recovery after precipitation of 10 micrograms of total yeast proteome extract. Lanes I-IV correspond to the cold acetone precipitation protocol as described above. Lanes V-VIII correspond to the chloroform/methanol/water (CMW) precipitation protocol, which was developed by D. Wessel and U. I. Flagge, Anal Biochem. 1984 April; 138(1):141-3. Four replicates for each protocol show reproducibility. The middle lane is a control (C), in which 10 μg of the yeast proteome is loaded. Comparing to the control lane, the two methods show similar banding patterns, both revealing relatively high protein recovery.

Recovery is quantitated for the two protocols in the following table (MP denotes membrane proteins. The number of protein identifications was determined through conventional 'bottom up' LC-MS/MS peptide sequencing. TMP denotes transmembrane proteins as determined from "GO" gene ontology annotations):

| Protocol | # total proteins | # unique proteins | # membrane proteins | # transmembrane proteins | % MPs | % TMPs | Recovery (%) |
|---|---|---|---|---|---|---|---|
| Acetone | 1,363 | 205 | 365 | 175 | 26.8 | 12.8 | 97 ± 4 |
| CMW | 1,451 | 293 | 402 | 197 | 27.7 | 13.6 | 79 ± 3 |

Based on these results, the acetone protocol given above has quantitatively superior recovery.

Example 15

Results of Precipitation and Resolubilization

Figure 12:
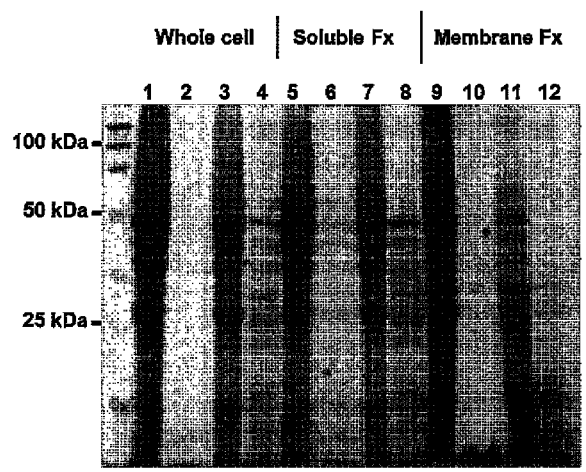

FIG. 12 is a coomassie stained SDS-PAGE gel, showing the results of acetone precipitation and proteome resolubilization with either 60% formic acid or water with 0.1% trifluoroacetic acid. Three sources of protein were used: (1) the whole cell extract of yeast, (2) the water-soluble protein fraction of yeast, and (3) a membrane protein fraction of yeast, as purified through ultracentrifugation. Lanes 1, 5, 9 are the original sample without precipitation. Lanes 2, 6, 10 are the remaining sample collected from the acetone solution following precipitation (the portion of the sample that does not precipitate). Lanes 3, 7, 11 are the redissolved pellet using formic acid, and lanes 4, 8, 12 are the redissolved pellet using 0.1% TFA in water. It can be seen that the portions of interest are purified as the procedure is performed across lanes 1-4, 5-8, and 9-12 respectively.

Example 16

Measure of Protein Recovery

Figure 13:
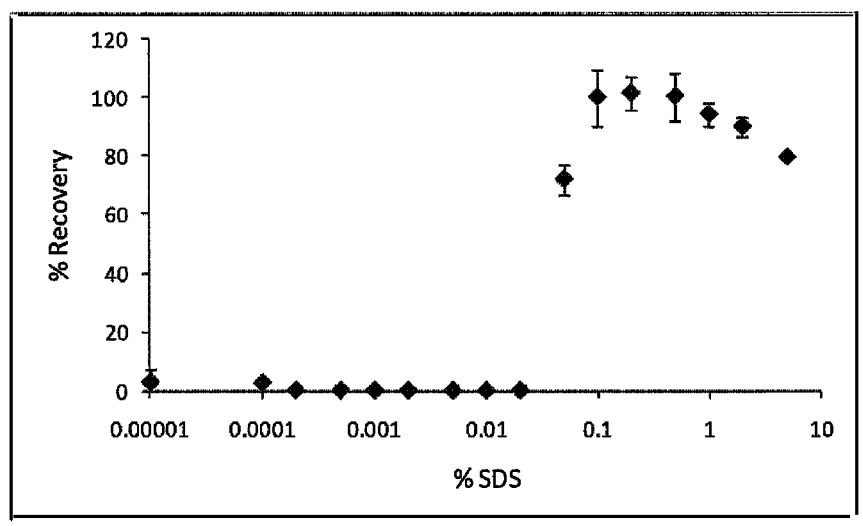
Figure 14:
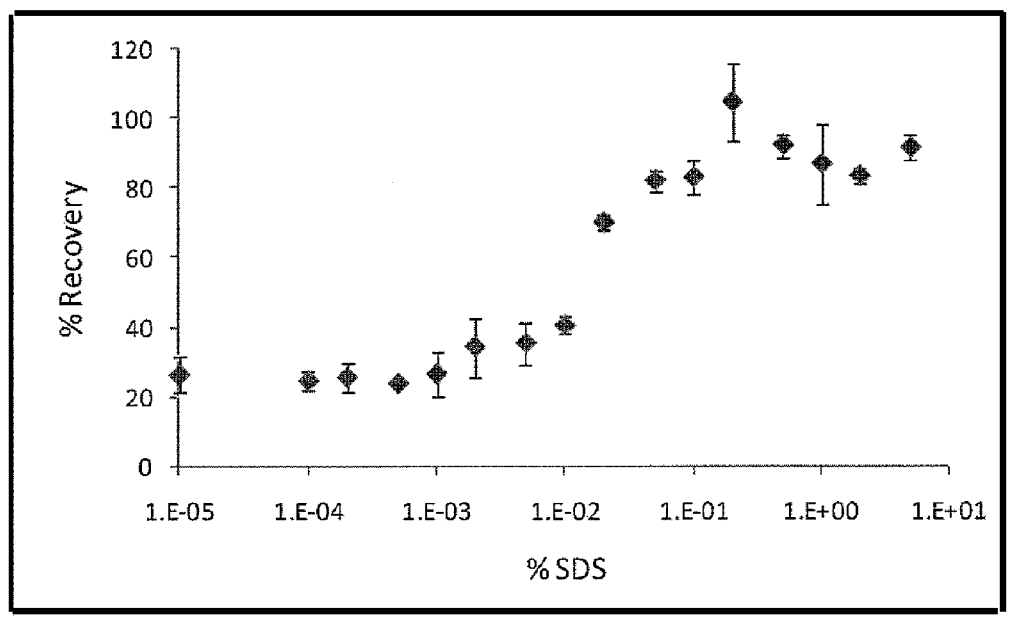

FIG. 13 shows protein recovery data following acetone precipitation, beginning with 100 micrograms of bovine serum albumin, BSA (1 g/L). The percent protein detected in the pellet is plotted as a function of the concentration of sodium dodecyl sulfate in the sample. As can be seen, the inclusion of SDS, between 0.1% to 1%, results in a protein recovery of approximately 100%. Less SDS in the sample results in very low recovery. FIG. 14 shows recovery of 10 micrograms of yeast (whole cell proteome extract) following acetone precipitation as a function of the % SDS in the original sample. As can be seen, the presence of SDS at a concentration of ~0.1% or higher improves protein yield.

Example 17

Proteome Recovery

Figure 15A:
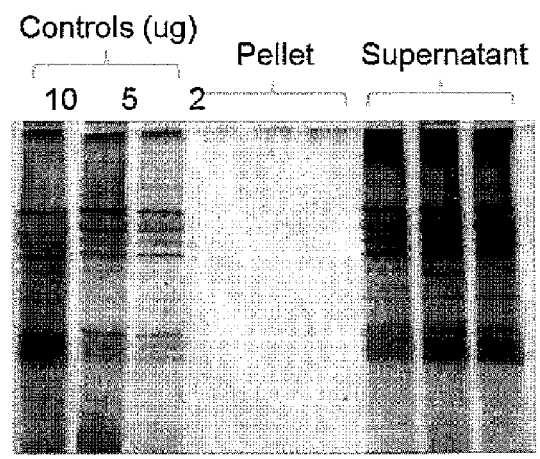
Figure 15B:
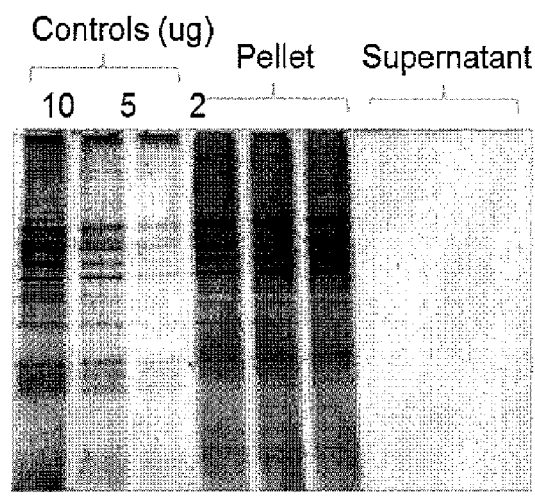

FIG. 15 shows proteome recovery through acetone precipitation in the presence or absence of SDS. FIG. 15(a) shows recovery of yeast proteins which were initially suspended in water, while FIG. 15(b) shows recovery of the same proteome mixture with inclusion of 0.1% SDS in the sample prior to acetone precipitation. The control lanes show the banding pattern from loading 10, 5, or 2 micrograms of protein. Approximately 10 micrograms of protein is seen in the pellet of (b) while all 10 micrograms are observed in the supernatant in (a) meaning that the sample did not precipitate.

Example 18

Protein Recovery Through Chloroform/Methanol/Water Protocol

Figure 16:
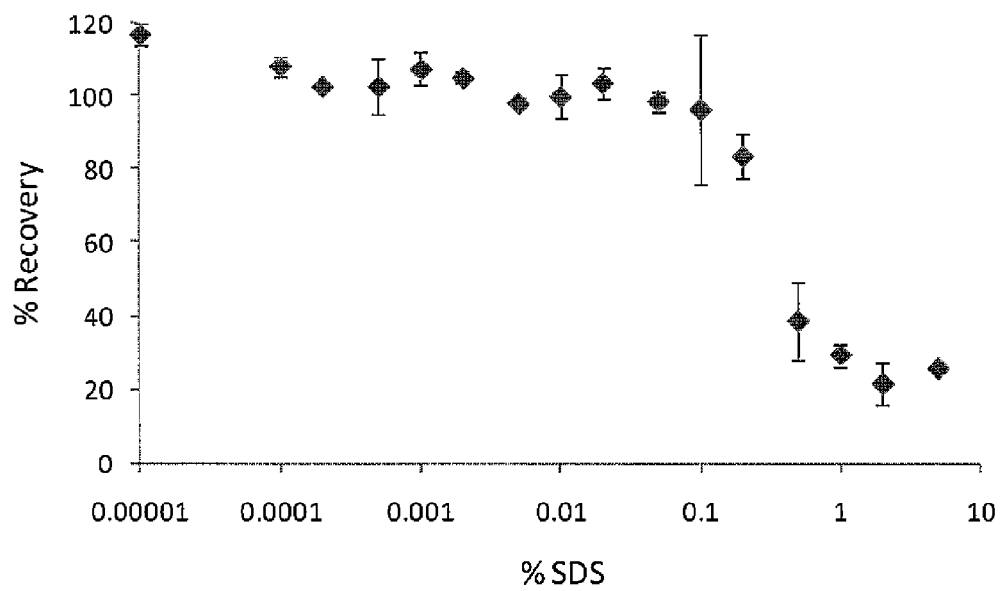

FIG. 16 shows protein recovery through chloroform/methanol/water precipitation. The sample was 10 micrograms of bovine serum albumin (100 microliters) prepared in water with varying concentrations of SDS. The recovery is approximately 100%, until the level of SDS in the sample becomes high. This level is dependent on the initial concentration of protein in the sample (i.e., more protein tolerates more SDS with high recovery).

Example 19

Effect of SDS on Electrospray Ionization LC-MS/MS

Figure 17A:
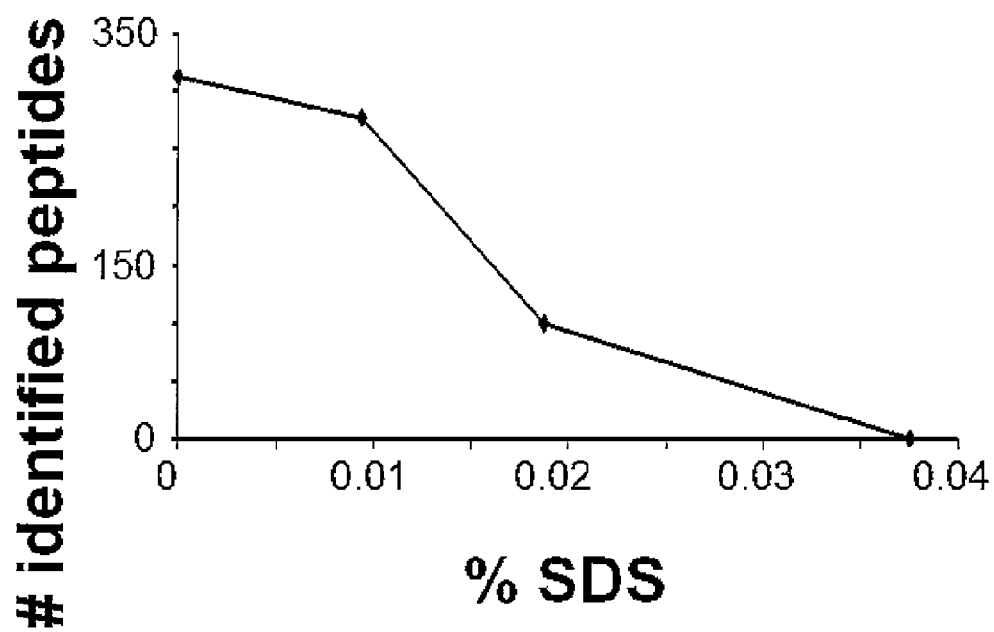
Figure 17B:
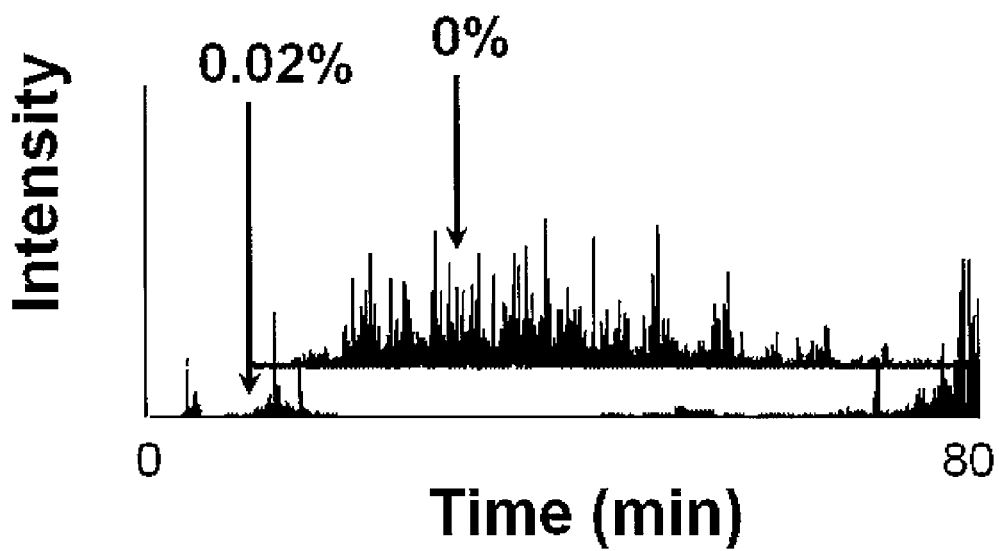

FIG. 17 shows that the detergent sodium dodecyl sulfate (SDS) causes severe signal suppression during LC-MS/MS with electrospray ionization. As seen in FIG. 18(a), the number of peptide identifications decreases significantly as the concentration of SDS in the injected sample increases passed 0.01%. The effect on the total ion chromatogram is clearly seen in FIG. 18(b) as both chromatographic traces are plotted along the same scaling in the y axis. Practically no signal is visible with 0.02% SDS in the sample. See D. Botelho, M. J. Wall, D. B. Vieira, S. Fitzsimmons, F. Liu, & A. A. Doucette; Top-Down and Bottom-Up Proteomics of SDS-Containing Solutions Following Mass-Based Separation. *J. Proteome Res.* 2010, 9, 2863-2870.

Example 20

Purification of Protein Containing SDS

Figure 18:
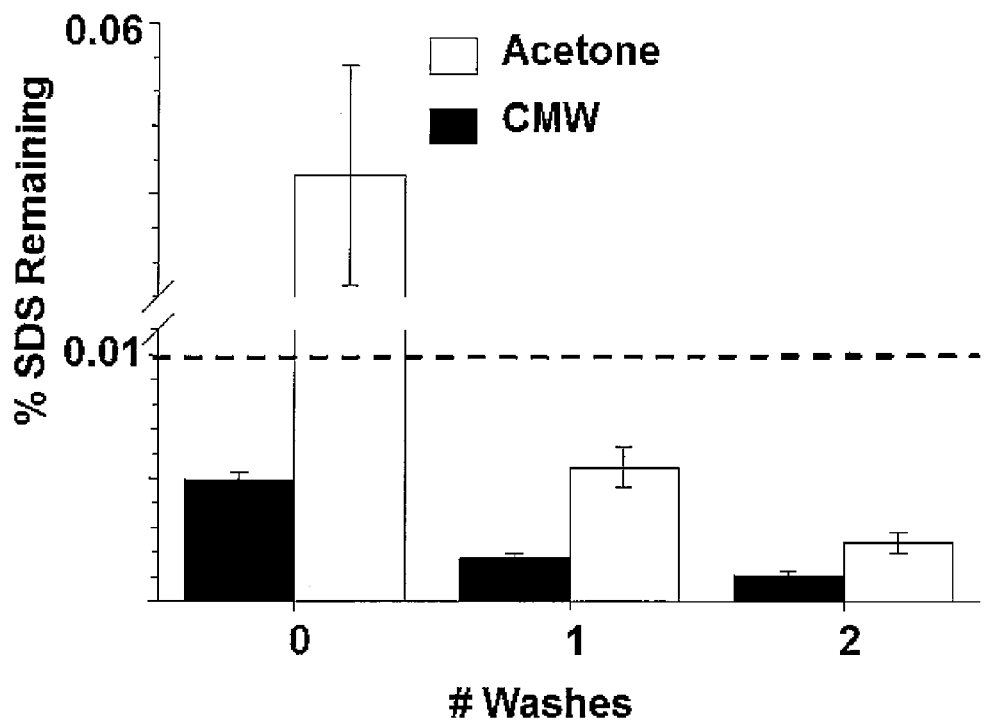

FIG. 18 shows the ability to purify a protein sample through acetone or chloroform/methanol/water (CMW) precipitation. A yeast proteome was spiked with 2% SDS; the percentage remaining assumes that the sample was brought back to the same initial volume. The conventional protocol for precipitation does not assume the addition of a wash protocol. (i.e., add more solvent—acetone or methanol in the case of CMW—then spin down the pellet again and remove the wash solvent). However, increasing the number of washes significantly enhances the purity of the protein product. The dotted line indicates the threshold for mass spectrometry (MS). See Botelho et al, as above.

Example 21

Resolubilization of Protein

Figure 19:
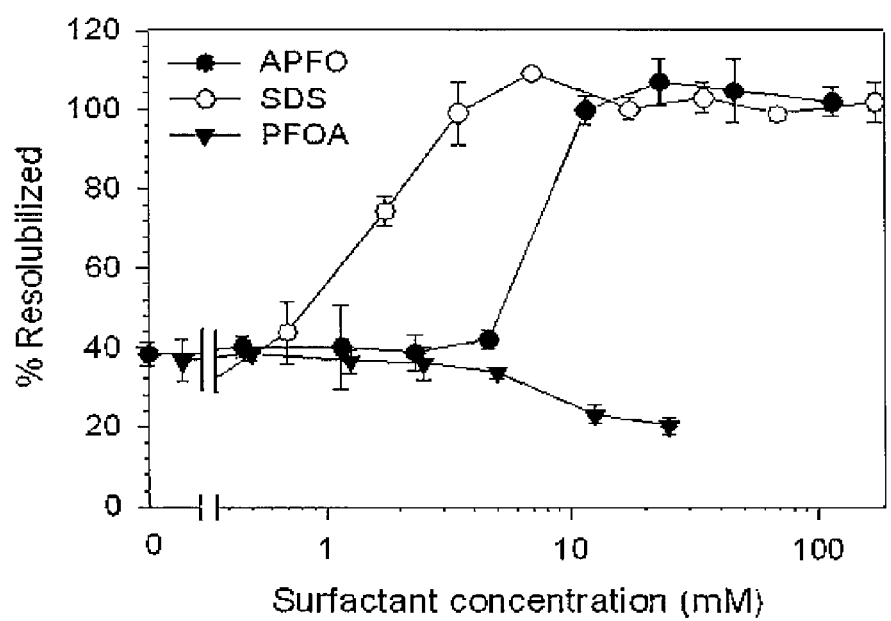

FIG. 19 shows the ability to resolubilize an acetone-precipitated protein pellet (yeast whole cell extract), illustrated using two three reagents—SDS (sodium dodecyl sulfate), APFO (ammonium perfluorooctanoate) and PFOA (perfluorooctanoic acid). Both APFO and PFOA are volatile reagents, so they can be eliminated from the sample through evaporation of the solution. As can be seen, APFO can effectively solubilize ~400% of the sample, through it requires a slightly higher concentration that SDS in order to do so. See D. B. Vieira, A. M. J. Crowell, & A. A. Doucette; Perfluorooctanoic acid and ammonium perfluorooctanoate: volatile surfactants for proteome analysis? Rapid Commun. Mass Spectrom. 2012, 26, 523-531.

Example 22

Resolubilization of Protein

Figure 20:
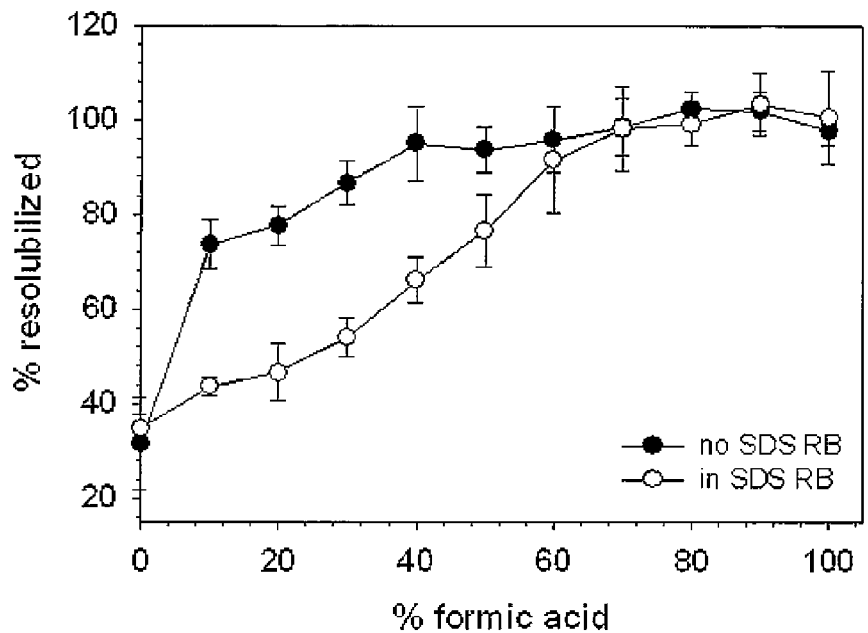

FIG. 20 shows the ability to resolubilize an acetone-precipitated protein pellet (yeast whole cell extract) is illustrated using formic acid. The yeast proteome was precipitated in the presence or absence of SDS in the reagent buffer (RB). 70% formic acid or higher will fully resolubilize the pellet. See Vieira, et al, as above.

Example 23

Peptide Recovery

Figure 21:
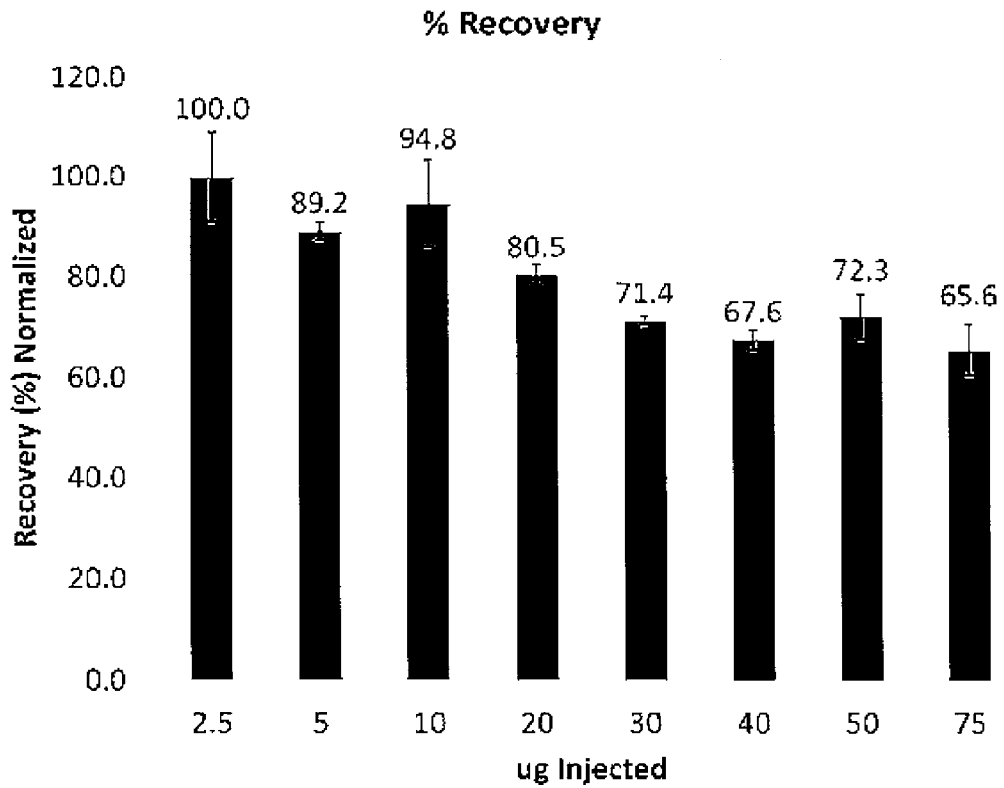

FIG. 21 shows peptide recovery data through reversed phase extraction. The sample was bovine serum albumin (BSA) which was digested with the enzyme trypsin. Varying amounts of the BSA peptides were loaded onto a reversed phase column (C18) as shown in the figure, and eluted using a stepwise gradient to 80% acetonitrile/0.1% TFA water. Peptide recovery remains high until 10 micrograms, above which the column begins to exceed its loading capacity.

Example 24

Recovery of Intact Protein

Figure 22:
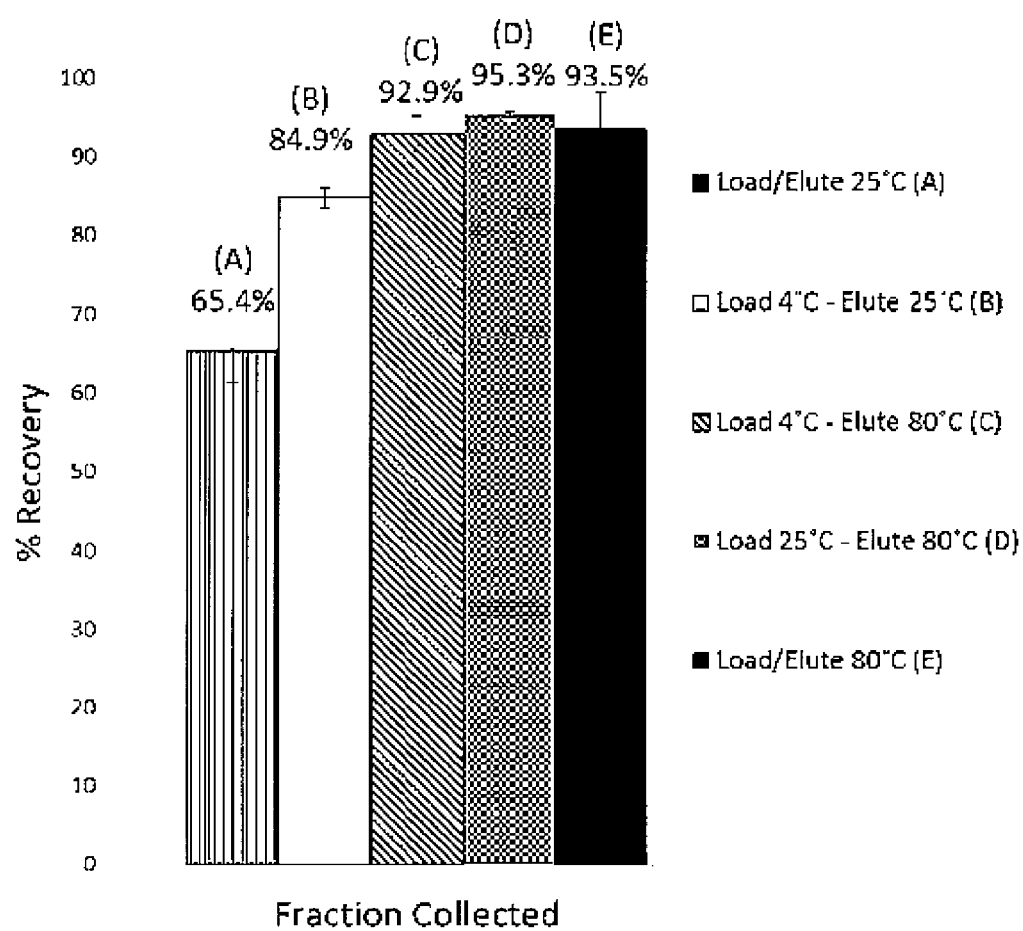

FIG. 22 shows intact (undigested) protein recovery data through reversed phase extraction. The sample was a whole cell extract of *E. coli* with approximately 7.5 micrograms loaded onto a reversed phase C18 column. The proteins were eluted using a rapid stepwise ramp to 80% acetonitrile. In a conventional (room temperature) load/elution protocol, significant protein loss is observed (recovery is only 65%). This recovery can be improved by modifying the loading and eluting temperatures of the reversed phase column (eg load at 4° C., elute at room temperature).

All patents, patent applications, and other publications referred to herein are hereby incorporated by reference.

The invention claimed is:

1. A method of centrifugation-aided filtration of solid components of interest comprising one or more of proteins, DNA, RNA, lipids, drugs and metabolites from a solution that also has solvent and soluble contaminants, the method comprising, in order,
   inserting a plug into a filtration cartridge to form a purification system in filtration mode, the filtration cartridge having a top opening, a bottom opening and a membrane covering the bottom opening so as to impede passage of the solid components of interest through the filtration cartridge and the plug being configured to be inserted into the bottom opening of the filtration cartridge, the plug having an extension that extends as high as the membrane and blocks all fluid flow out of the filtration cartridge even during centrifugation, so that no filtration occurs;
   adding the solution into the top opening of the filtration cartridge;
   incubating the solution within the purification system in filtration mode;
   placing the purification system in a centrifuge tube such that the purification system overhangs a top of the centrifuge tube;
   centrifuging the purification system in filtration mode;
   removing the plug from the filtration cartridge;
   and centrifuging the filtration cartridge, such that the solid components of interest are retained on the membrane and the solvent and soluble components are filtered through the membrane.

2. A method of extraction using an extraction cartridge having a top opening and charged with solid phase extraction materials, the method comprising performing the method of claim 1, then
   inserting the plug into the bottom opening of the filtration cartridge;
   solubilizing the solid components of interest within the filtration cartridge with a solubilizing reagent;
   removing the plug from the filtration cartridge;
   inserting the bottom opening of the filtration cartridge into the top opening of the extraction cartridge to form a purification system in extraction mode; and
   extracting a purified protein from the solid components of interest by elution through the extraction cartridge of the system in extraction mode.

3. The method of claim 2 where extracting a purified protein from the solid components of interest further comprises one or more cycles of adding eluting solvent and centrifuging the purification system in extraction mode, in which the solid components of interest elute through the purification system in to the centrifuge tube.

* * * * *